United States Patent [19]

Powell

[11] Patent Number: 5,399,401
[45] Date of Patent: Mar. 21, 1995

[54] FLEXIBLE, LOW HAZE CHLORINE-FREE ETHYLENE COPOLYMER ARTICLE

[75] Inventor: Richard J. Powell, Orange, Tex.

[73] Assignee: E. I. Du Pont de Nemours and Company, Wilmington, Del.

[21] Appl. No.: 200,809

[22] Filed: Feb. 22, 1994

Related U.S. Application Data

[63] Continuation of Ser. No. 962,752, Oct. 19, 1992, abandoned.

[51] Int. Cl.$^6$ .............................................. C08K 5/20
[52] U.S. Cl. ............................. 428/36.9; 428/220; 524/210; 524/229; 524/230; 525/296
[58] Field of Search ............... 428/36.9, 220, 36.9; 524/210, 229, 230; 525/296; 526/318.45

[56] References Cited

U.S. PATENT DOCUMENTS

| | | | |
|---|---|---|---|
| Re. 32,325 | 1/1987 | Smith | 524/229 |
| 3,249,570 | 5/1966 | Potts | 525/221 |
| 3,796,775 | 3/1974 | Glaser et al. | 260/897 B |
| 3,821,179 | 6/1974 | Powell | 260/88.1 R |
| 3,865,776 | 2/1975 | Gergen | 260/336 AQ |
| 3,869,338 | 3/1975 | Kavesh | 428/36.9 |
| 4,198,983 | 4/1980 | Becker et al. | 128/349 R |
| 4,663,383 | 5/1987 | Lowe | 524/493 |
| 4,751,262 | 6/1988 | McKinney | 524/232 |

FOREIGN PATENT DOCUMENTS 58-050965 3/1983 Japan.
59-199749 11/1984 Japan.

*Primary Examiner*—David Buttner
*Attorney, Agent, or Firm*—Craig H. Evans

[57] ABSTRACT

Highly flexible articles having wall thickness of at least 0.01 inches are made from chlorine-free direct ethylene copolymers containing small amounts of selected known slip additives. Articles in the form of tubes or tubing have particular utility for replacement of PVC based tubing used in medical applications.

9 Claims, No Drawings

FLEXIBLE, LOW HAZE CHLORINE-FREE ETHYLENE COPOLYMER ARTICLE

This is a continuation of application Ser. No. 07/962,752, filed Oct. 19, 1992, now abandoned.

FIELD OF THE INVENTION

This invention relates to chlorine-free, plasticizer-free flexible articles having a wall thickness of at least 0.010 inches. More particularly, it relates to articles melt fabricated from ethylene copolymers melt-blended with certain secondary amides. An important embodiment is medical tubing or sheeting, particularly respiratory tubing.

BACKGROUND OF THE INVENTION

Flexible articles such as tubing and sheeting, particularly those used in medical applications, can be made from a number of materials.

U.S. Pat. No. 3,796,775, while not teaching medical utility, does teach that molded articles such as tubing can be made from a composition having environmental stress-crack resistance and low-temperature impact strength. The composition taught is a homogeneous mixture of polyethylene, polyisobutylene or an ethylene/vinyl acetate copolymer, and N,N'-disteroylethylenediamine (N,N'-ethylene-bis-stearamide).

U.S. Pat. No. 4,198,983 teaches catheters made from a block copolymer having thermoplastic rubber characteristics with a central rubbery polyolefin block and terminal blocks of polystyrene and, optionally, cross-linked organic silicone and polypropylene. A hydrophobic oil-type plasticizer is added to provide softness. It teaches that in certain circumstances, cured silicone elastomers and fatty acid amides, together, provide reduced surface friction over that contributed by either ingredient alone.

U.S. Pat. No. 3,865,776 teaches kink-resistant tubing having a useful degree of clarity that is a combination of two types of block polymers, mineral white oil, high-melt-flow polypropylene and a resin. Each of the two block pollers has at least two monoalkenylarene and at least one substantially completely hydrogenated conjugated diene polymer block. They differ in molecular weight and monoalkenylarene polymer block content. The resin serves as a flow promoter and is compatible with either the monoalkenylarene or the diene polymer blocks. Examples of useful resins are ethylene/vinyl acetate copolymer and a copolymer of vinyl toluene and alpha-methylstyrene.

Non-cross-linked thermoplastics, especially polyvinyl chloride (PVC) containing large amounts of plasticizer, have found acceptance in a number of medical applications. PVC has, in deed, become the material of choice particularly for applications where transparency is required such as in respirator tubing. This is because its properties generally far exceed those needed for the various medical applications and it is inexpensive. Properties generally desired in medical tubing and sheeting applications where PVC has found utility are clarity or transparency (low haze), flexibility (drape), kink resistance, adequate burst strength, low surface tackiness, scratch resistance, and bondability to connectors.

Japanese Patent Publication J5-8050965 discloses a resin that has excellent transparency, softness, and resiliency and is therefore applicable to the manufacture of medical instruments such as catheters, blood bags and tubes. The resin employs vinyl-chloride-based resins blended with ethylene/vinyl acetate/carbon monoxide copolymer, low molecular weight plasticizers such as dioctyl phthalate, magnesium or calcium oxide, stabilizers such as calcium stearate and a bisamide.

Japanese Patent Application J5-9199749 discloses a somewhat similar resin for use in blood bags, tubes and the like. It is an ethylene-vinyl acetate/vinyl chloride graft copolymer blended with dicarboxylic acid amide. Surface stickiness is reported as being greatly reduced by the acid amide. Calcium-zinc stabilizers and epoxidized soybean oil are used with the graft copolymer and acid amide in the example.

While PVC has been preferred over other known polymers in many medical applications, PVC does present some problems. There is concern over possible health risks from plasticizers such as the dioctyl phthalate typically used in PVC. Environmentally, chlorine containing polymers are undesirable. With increased concern over disposal of medical waste, many hospitals now incinerate waste containing PVC. The corrosive incineration products that result must be handled. Many existing incinerators are not equipped with adequate scrubbers and are not made of adequately corrosion-resistant material.

What is needed, then, is a replacement for PVC that does not pose the environmental concerns of PVC, does not produce corrosive incineration products (does not contain chlorine) and does not require the addition of potentially hazardous plasticizers to obtain the properties desired. It must at the same time have properties sufficiently close to those of PVC to satisfy the needs of the medical community for clarity or transparency (low haze), flexibility (drape), kink resistance, adequate burst strength, low surface tackiness, scratch resistance, and bondability to connectors.

Multi-layer tubing and sheeting has now been found that can achieve the balance of properties needed, but these are difficult to manufacture and are relatively expensive. Coextrusion requires special equipment and bonding the layers together can be difficult. Recycle problems are presented when layers are made of different materials. Separating the components is difficult, and chipping them together is not practical, unless there is a use for the blend of components. Thus, the tubing or sheeting should preferably be of a single layer construction. It should be easily processible, preferably on the same equipment (molding, extrusion, assembly equipment and the like) as the PVC it replaces.

Ethylene copolymers have good flexibility without the need for plasticizers due to the nature of their polymeric structure. They have low crystallinity because of high levels of comonomer. They are, however very tacky and, thus, present handling problems.

Tackiness in some polymers can be reduced by incorporating certain antiblocking or "slip" agents into the polymer. These slip agents exude to the surface and reduce tackiness. Many types of slip agents are known. They include fatty acids or fatty acid derivatives such as esters, alcohols, metallic salts and amides. There is a vast range of primary amides, primary bisamides, secondary amides and secondary bisamides derived from saturated or unsaturated mono or diacids and amines. *Modern Plastics Encyclopaedia* lists many such materials.

With respect to ethylene copolymers, slip agents have found principal utility in reducing blocking tendencies in pellets and in thin films, particularly for packaging. On exudation, they are known to cause chalkiness, haze and loss of transparency.

U.S. Pat. No. 32,325 teaches incorporating 0.01 to 1 wt. % of a di-secondary bisamide selected from N,N'-ethylene-bis-oleamide; N,N'-ethylene-bis-erucamide; N,N'-dioleyl adipamide; and N,N'-dierucyl adipamide in a wide range of ethylene copolymer pellets. Flexibility, transparency and other properties desired in the present invention are neither taught nor suggested for the pellets or products made therefrom.

U.S. Pat. No. 3,821,179 teaches incorporating 0.05 to 2 wt. % N,N'-dierucyl adipamide or N,N'-dierucyl sebacamide as a slip agent in thin films and coatings of ethylene copolymer ionomer. Ethylene bipolymer ionomer films up to 2 mil (0.002 inches) thick are described. Only the above two agents are taught as suitable for reducing blockiness while still maintaining low chalking and good optical properties. Exudation of slip agent to the surface of these thin films is sufficiently rapid to provide reduced blocking. There is no suggestion of use in articles having thicker cross-section and no suggestion that the balance of properties needed for medical applications can be achieved.

SUMMARY OF THE INVENTION

The present invention provides for an excellent replacement of PVC in flexible articles, particularly those used in medical applications. Particularly, there is provided flexible articles having a thickness of at least 0.01 inches made from chlorine-free, direct ethylene copolymers having a flexural modulus of 2000–7000 pounds per square inch (psi) melt-blended with an effective amount, preferably 0.1 to 0.8 weight percent (wt. %), of a secondary amide selected from the group consisting of N,N'-ethylene-bis-oleamide, N,N'-dierucyl adipamide and N-erucyl erucamide. Preferably, no plasticizers are added to the melt-blend. Preferred ethylene copolymers are ethylene vinyl acetate bipolymers having 25 to 35 wt. %, preferably 30 to 35 wt. %, vinyl acetate, and ethylene/alkyl acrylate/(meth)acrylic acid terpolymers containing 15 to 30 wt. %, preferably 20 to 25 wt. %, acrylate and 5 to 15 wt. %, preferably 5 to 10 wt. %, acid, as well as ionomers derived from these copolymers.

DETAILED DESCRIPTION OF THE INVENTION

In this disclosure, the term copolymer embraces polymers with two or more monomers. Where it is necessary to make a distinction between the number of comonomers in a polymer, the polymers are referred to as bipolymers, terpolymers, and the like. The term "direct copolymer" describes a polymer made by polymerizing all monomers together. These differ from "graft copolymers" in which a second comonomer is grafted onto as existing polymer.

The articles of the invention may be tubes or tubing, sheet or sheeting, produced by extrusion, or products derived from these such as formed sheet, containers and the like. Preferably the articles are tubes or tubing.

Properties can be obtained by using multi-layered tubes, but this is undesirable due to issues such as cost and recycle concerns. What is desired then is a single layer tube that has the proper properties to be useful in the end application. Preferably the properties of the tubes should approach that of PVC, but it is recognized that, since the properties of PVC generally exceed those that are needed, the tubing can have subjectively lower properties so long as the proper balance is achieved.

It must be emphasized that a balance of properties is needed. For example, for tubes, good kink resistance is desirable, and so is drape, which is generally associated with low stiffness. Tube clarity is important and so is low tackiness and coefficient of friction. Increased flexibility is achieved at higher comonomer levels, but this will alter the solubility of any slip additives incorporated. More additive may produced less tackiness, but is more likely to result in haze development.

Quantitative measurement of the important properties is difficult if not impossible. What has been found, however, is that the tubing or sheeting is acceptable if it meets the preferred conditions described below, even though subjective.

Clarity of plaque samples (described below in the examples) can be measured by an ASTM D-1003 haze test. These readings are representative of what can be expected when the polymer melt-blend is used to make, for example, a tubing sample. Lower readings are indicative of higher clarity. Readings of up to 30 are acceptable. Preferably, readings should be 25 or lower. Still, more preferably haze readings of less than 20 are desired particularly as measured shortly after manufacture.

A better analysis of clarity, particularly of tubing samples, can be determined subjectively by comparison to clarity of PVC tubing. Observers are requested to evaluate the sample on a 1 to 10 scale, PVC being rated at 10. Preferably, the clarity of tubing should be in a range of 5 to 10, more preferably 7 to 10 and still more preferably 8 to 10.

While some deterioration in clarity may occur on aging, it is important that reasonable clarity be retained upon aging of the finished product. Preferably, readings should be within the above preferred ranges after at least 1 month. Retention of clarity for longer storage periods at ambient temperatures and elevated temperature are preferred.

Surface tackiness is an important factor affecting the handleability of tubing. The more tacky, the less handleable. No good quantitative test is known for tackiness or surface friction. Handleability of plaques in this case is subjectively measured on a scale of 1 to 3, 3 being the most handleable, which is essentially the least tacky. Handleability of plaques should be at least 2, preferably 3. Handelability in tubing, as apposed to plaques, is subjectively measured in comparison to PVC tubing. For tubing, a scale of 1–10 proved convenient, PVC being assigned a rating of 10. Preferably, tube handleability should be 5–10, more preferably 7–10 and still more preferably 8–10.

Flexural modulus of plaques, determined by ASTM D-790, preferably is in the range of 2000 to 7000 psi. Higher moduli within the range would be expected to produce a stiffer tube with poorer drape properties. Kink resistance appears to be related to a variety of factors, modulus being only one. While it has been possible to arrive at a measure of kink resistance, it has not been possible to correlate it with a specific tensile, flexural or composition characteristic. A balance is needed. Lower moduli produce a tube that has better drape properties. The preferred drape and kink resistance can best be measured in tubing samples made from the material used to make the plaques.

Drape is not a critical measurement. It will vary with tubing geometry (diameter, wall thickness, whether it has a smooth bore or a crush-resistant lumen, etc.) but should be comparable to PVC tubing having the same geometry. Stiffer tubing is acceptable for some applications. For example, pressure lines and other tubing applications that do not directly attach to respiratory masks can be stiffer.

Kink resistance is important yet there is no standard test or quantitative measurements of satisfactory kink resistance. Using the test described below, higher distance of travel of the Instron tester before kinking results are preferred. Using the 3½ inch long tube, travel before kinking should be at least 1.2 inches, more preferably 1.4 inches, and still more preferably 1.6 inches.

The resulting tube must be easily bondable to connectors and other fittings. Typically this is done by dipping the end of the tube into a suitable solvent, then inserting the tube end into the connector and allowing it to dry. Sheeting material used in blood bags, urine bags and the like must be puncture resistant. It may be desirable to add colored pigment.

With the present invention, it has been found that certain chlorine-free, direct ethylene copolymers are useful in producing flexible articles having a thickness of at least 0.01 inches meeting the above needs, particularly providing the balance of clarity and tackiness and of drape and kink resistance desired particularly for medical applications without the addition of plasticizers. They have a flexural modulus, as measured by ASTM D-790, of 2000 to 7000 psi. The preferred copolymers are ethylene vinyl acetate bipolymers having 25 to 35 wt. %, preferably 30 to 35 wt. %, vinyl acetate, and ethylene/alkyl acrylate/(meth)acrylic acid terpolymers containing 15 to 30 wt. %, preferably 20 to 25 wt. %, acrylate and 5 to 15 wt. %, preferably 5 to 10 wt. %, acid, as well as ionomers derived from these copolymers. Preferred acrylates in the terpolymers are n-butyl acrylate and isobutyl acrylate. The preferred acids are acrylic acids and methacrylic acid. Low modulus ionomers are described in U.S. Pat. No. 4,690,981. Methods for preparing the ethylene copolymers of this invention are well known to those skilled in the art.

The ethylene copolymers are melt-blended with an effective amount, preferably about 0.1 to 0.8 wt. %, more preferably about 0.1 to 0.5 wt. %, and still more preferably about 0.1 to 0.3 wt. %, of a secondary amide selected from the group consisting of N,N'-ethylene-bis-oleamide, N,N'-dierucyl adipamide and N-erucyl erucamide. Preferably, no plasticizers are added to the melt-blend. It has been found that the preferred slip agent for the ethylene/vinyl acetate bipolymer is N-erucyl erucamide, preferably at a loading of about 0.3 wt. %, and for ethylene/alkyl acrylate/acid terpolymer is N,N'-ethylene-bis-oleamide, preferably at loading of about 0.3 wt. %.

The blending may be done by any well known method for melt-blending. The slip agent may be added as part of the process for making the copolymer, that is, it can be added prior to pelletizing. Alternatively, it may be added to the pellets and then melt-blended in a roller mill, extruder, or other well known melt-blending equipment. Preferably, the melt-blend is homogeneous.

TESTS

Burst Test

One end of a tubing sample was attached to a pressure source, the other end of the tube being sealed. Pressure was gradually increased to 100 psig and held for a sufficient time to assure that this minimum acceptable burst pressure can be met. The pressure was then increased slowly until the tubing failed. Preferably, failure should not occur at pressures lower than 125 psig, more preferably at pressures lower than 135 psig.

Kink Test

A 3½ inch length of tubing (sample)was attached to special mounting plates designed to allow a flow of gas to enter into one end and exit to atmosphere at the other end. The mounted sample was placed into the jaws of a Instron tester. A 5 liter per minute flow of gas from a 2 psig source was started through the sample, and then the instron was started at a head speed of 50 millimeters per minute. Pressure of the gas feed was measured. When a sudden increase in pressure (pressure spike) was observed indicating that the sample had kinked, the instron was stopped and the compressive force and distance compressed were recorded. Good kink resistance is indicated by higher distances compressed. Compressive force provides some indication of tubing stiffness. Better drape is expected at lower compressive force.

Clarity and Tackiness Tests of Plaques and Tubing

Clarity of plaque samples is the inverse of haze which is measured using ASTM D-1003. Clarity of tubing and the tackiness of both plaques and tubing are subjective measurements. As discussed above, observers were requested to evaluate plaque handling (lack of tackiness) on a scale of 1 to 3, 3 being the best. Other observers were requested to evaluate both clarity and handling of tubing on a 1 to 10 scale, 10 being comparable to PVC.

| PLAQUE EXAMPLES The amides used in the plaque examples were as follows: | |
|---|---|
| Amide 1 | N-Erucyl Erucamide |
| Amide 2 | N-Oleyl Erucamide |
| Amide 3 | Stearamide |
| Amide 4 | N,N'-di-Erucyl Adipamide |
| Amide 5 | N-Oleyl Palmitamide |
| Amide 6 | N,N'-Ethylene-bis-oleamide |

EXAMPLE 1

Ethylene/n-butyl acrylate/methacrylic acid (E/n-BA/MAA) having a weight percentage of monomers of 67.5/23.5/9 and a melt index, using ASTM 1238, of 25 g/10 minutes, was, in general, melt-blended with the amides listed in Table 1 on a laboratory roll-mill at a temperature of 160 deg. C. for 10 minutes. Samples 8a and 8b were made by adding the amine in-line during the manufacturing process prior to pelletizing the E/n-BA/MAA. The resulting blends were compression molded into plaques having a thickness of 40 mils (0.04 inches). Results of the ASTM D-1003 haze test and the subjective assessment of tackiness for the ethylene terpolymer and for the terpolymer blended with different amides at different concentrations as indicated are presented in Table 1. Percent haze was measured after storage of samples at ambient temperature (about 23° C.) for 1 day, 1 week and 1 month periods after blending. Handling (reduction in tackiness) was assessed after 1 week, but did not vary significantly from 1 day to one month. Flexural modulus, measured using ASTM D-790 was 3.7 Kpsi.

N-oleyl erucamide, stearamide and N-oleyl palmitamide did not improve handling significantly, (reduce tackiness), despite exudation sufficient to cause considerable haze.

As can be seen from Table 1, Samples 7 and 8, particularly 7a and 8a, using N,N'-ethylene-bis-oleamide, yielded the best combination of desired properties.

TABLE 1

Properties of Blends of E/nBA/MAA and Amides

| Sample | Amide | Wt. % | Haze % 1 Day | 1 Week | 1 Month | Handling |
|---|---|---|---|---|---|---|
| 1 | None | 0 | 10 | 14 | 21 | 1 |
| 2a | 1 | 0.3 | 10 | 15 | 25 | 1 |
| 2b | 1 | 0.5 | 15 | 36 | 78 | 2 |
| 3a | 2 | 0.3 | 10 | 19 | 35–55 | 1 |
| 3b | 2 | 0.5 | 10 | 11 | 17–43 | 1 |
| 4a | 3 | 0.3 | 8 | 20 | 35 | 1 |
| 4b | 3 | 0.5 | 9 | 26 | 48 | 1 |
| 5a | 4 | 0.3 | 13 | 33 | 49 | 2 |
| 5b | 4 | 0.5 | 15 | 29 | 45 | 2 |
| 6a | 5 | 0.3 | 13 | 18 | 40 | 1 |
| 6b | 5 | 0.5 | 8 | 22 | 55 | 1 |
| 7a | 6 | 0.3 | 6 | 7 | 10 | 3 |
| 7b | 6 | 0.5 | 14 | 21 | 34 | 3 |
| 8a | 6 | 0.27 | 9 | 14 | 20 | 2 |
| 8b | 6 | 0.44 | 12 | 21 | 24 | 2 |

EXAMPLE 2

Ethylene/vinyl acetate (EVA) having a weight percentage of vinyl acetate of 33% and a melt index, using ASTM D-1238, of 43 was melt-blended with the amides listed in Table 2 on a laboratory roll-mill at a temperature of 160 deg. C. for 10 minutes. The resulting blends were compression molded into plaques having a thickness of 40 mils (0.04 inches). Results of the ASTM D-1003 haze test and the subjective assessment of tackiness for the ethylene terpolymer and for the terpolymer blended with different amides at different concentrations as indicated are presented in Table 2. Percent haze was measured after storage of samples at ambient temperature (about 23° C.) for 1 day, 1 week and 1 month periods after blending. Handling was assessed after 1 week, but at this temperature varied little over a month. Flexural Modulus of the ethylene vinyl acetate polymer was not measured, but is about 3.2 Kpsi.

N-oleyl palmitamide and N-oleyl erucamide showed no improvement in handling, and stearamide produced high haze.

As can be seen from Table 2, Samples 10, using N-erucyl erucamide yielded the best combination of desired properties with Samples 15, using N,N'-ethylene-bis-oleamide, yielding the next best. Among the three suitable secondary amides, it appears that different ones may be most suitable for different polymers.

TABLE 2

Properties of Blends of EVA and Amides

| Sample | Amide | Wt. % | Haze % 1 Day | 1 Week | 1 Month | Handling |
|---|---|---|---|---|---|---|
| 9 | None | 0 | 8 | 14 | 15 | 1 |
| 10a | 1 | 0.3 | 15 | 16 | 17 | 2 |
| 10b | 1 | 0.5 | 19 | 21 | 28 | 3 |
| 11a | 2 | 0.3 | 15 | 21 | 24 | 1 |
| 11b | 2 | 0.5 | 11 | 18 | 22 | 2 |
| 12a | 3 | 0.3 | 12 | 47 | 76 | 2 |
| 12b | 3 | 0.5 | 7 | 87 | 96 | 3 |
| 13a | 4 | 0.3 | 27 | 28 | 28 | 1 |
| 13b | 4 | 0.5 | 41 | 42 | 43 | 1 |
| 14a | 5 | 0.3 | 12 | 15 | 16 | 1 |
| 14b | 5 | 0.5 | 5 | 7 | 11 | 1 |

TABLE 2-continued

Properties of Blends of EVA and Amides

| Sample | Amide | Wt. % | Haze % 1 Day | 1 Week | 1 Month | Handling |
|---|---|---|---|---|---|---|
| 15a | 6 | 0.3 | 17 | 23 | 23 | 2 |
| 15b | 6 | 0.5 | 41 | 44 | 47 | 2 |

Procedure for making tubing

Tubing samples used in the tests were extruded to a nominal internal diameter of 0.18 inches and a nominal wall thickness of 0.04 inches using standard extrusion conditions into a water quench bath. Heat settings in the first two zones of the 2 inch extruder were 275° C. and in the third zone, at the die and gate were 300° C. The screw was operated at 65 RPM. Puller speed was 109 feet per minute.

No attempt to optimize extruder conditions was made, but it is believed that some optimization could result in better tubing properties than were exhibited in the following examples. For example, both extrusion and quench temperatures can be varied, different quench fluids can be employed, the rate of extrusion and the rate and amount of pull on the exiting extruded material can be varied, and different die and pin or bullet configurations can be used. One skilled in the art of extrusion will be able to, with limited experimentation optimize the extrusion process.

EXAMPLE 3

Tubing samples were produced using the polymer blend of 8a. Using the tests described above, 30 samples were tested to determine burst pressure at ambient temperature. All samples passed the 100 psi test. The average burst pressure was 143 psi with a standard deviation of 5.58. Three samples selected at random were tested using the kink test described above. The results were compression forces of 0.64 pounds, 0.65 pounds and 0.60 pounds. The corresponding distances of travel before kinking were 1.44 inches, 1.51 inches and 1.87 inches. Handling was good, that is to say tackiness was low and the tubing has retained a reasonable clarity for over 6 months. E/nBA/MAA terpolymer without slip additive had an average compression force of 2.33 pounds (standard deviation of 0.15) and a travel distance before kinking of 1.35 inches (standard deviation of 0.11).

EXAMPLE 4

Tubing samples of PVC, Sample 1 (E/nBA/MAA without slip agent), Sample 8b, and samples made by melt-blending 8b with additional E/nBA/MAA to produce Sample 8c (E/nBA/MAA terpolymer loaded with 0.30% N,N'-ethylene-bis-oleamide) and Sample 8d (E/nBA/MAA terpolymer loaded with 0.20% N,N'-ethylene-bis-oleamide) were evaluated. A number of samples were observed by panels of different sizes after storage at ambient temperature (23° C.) for the times indicated in Table 3 and at 40° C. for times indicated in Table 4. Samples were stored in both in darkness (no-light conditions) and in room light. No difference was seen in results based on lighting. The Values for the PVC control represent the goal values of 10 for clarity and 10 for handling.

The first sample with no amide shows good clarity after seven months, but poor handling. At ambient temperatures, samples 8b, 8c and 8d, show excellent handling, and good clarity except for the highest level of additive (Sample 8b). Storage at 40 deg. C. indicated good clarity and handling even after extended storage for all samples containing additive. Storage at 50° C. resulted in all samples (1, 8b, 8c, and 8d) having the same ratings after 2 months. That is while clarity improved to the level of Sample 1 handling deteriorated, that is to say tackiness increased to the level of Sample 1. Thus, while storage at 23° and 40 deg. C is possible, storage at 50 deg. C causes increased tackiness.

TABLE 3

Effect of Aging at 23 deg. C. on Clarity and Handling

| Sample | Clarity/Handling after: | |
|---|---|---|
| | 2 weeks | 7 months |
| PVC control | 10/10 | 10/10 |
| 1 | 6.0/6.3 | 8.0/5.0 |
| 8b | 5.7/8.5 | 4.0/8.0 |
| 8c | 8.2/9.5 | 8.0/9.0 |
| 8d | 8.0/7.7 | 8.0/9.0 |

TABLE 4

Effect of Aging at 40 deg. C. on Clarity and Handling

| Sample | Clarity/Handling after: | |
|---|---|---|
| | 2 weeks | 6 + 1* |
| PVC control | 10/10 | 10/10 |
| 1 | 6.7/5.7 | 8.0/4.0 |
| 8b | 9.0/9.6 | 8.0/9.0 |
| 8c | 8.0/8.3 | 8.0/8.0 |
| 8d | 7.7/7.3 | 8.0/7.0 |

*6 months aging at 40 and 1 month aging at 23 deg. C.

I claim:

1. A flexible, low haze, article prepared from a composition, the composition comprising:
   a) a chlorine-free ethylene/alkyl acrylate/(meth)acrylic acid copolymer or ionomer thereof, said copolymer or ionomer thereof having a flexural modulus of about 2000–7000 psi, and
   b) a sufficient amount, in the range of about 0.1–0.8 weight percent, based on the weight of the copolymer, of a secondary amide selected from the group consisting of N,N'-ethylene-bis-oleamide, N-oleyl erucamide, and N-erucyl erucamide to provide good handleablity and a percent haze of less than 35 as measured using ASTM D-1003 on a plaque stored at ambient temperature for at least one month, the article having a thickness of at least about 0.01 inches.

2. The article of claim 1, wherein the ethylene/alkyl acrylate/(meth)acrylic acid copolymer (a) contains about 15–30 weight percent alkyl acrylate and about 5–15 weight percent acrylic or methacrylic acid.

3. The article of claim 2, wherein the alkyl acrylate is n-butyl acrylate and the acid is methacrylic acid.

4. The article of claim 3, wherein the secondary amide (b) is N,N'-ethylene-bis-oleamide.

5. The article of claim 4 in the form of tubes or tubing.

6. A flexible, low haze, article prepared from a composition, the composition comprising:
   a) a chlorine-free ethylene/vinyl acetate copolymer having a flexural modulus of about 2000–7000 psi, and
   b) a sufficient amount, in the range of about 0.1–0.8 weight percent, based on the weight of the copolymer, of a secondary amide selected from the group consisting of N-oleyl erucamide and N-erucyl erucamide to provide good handleablity and a percent haze of less than 35 as measured using ASTM D-1003 on a plaque stored at ambient temperature for at least one month, the article having a thickness of at least about 0.01 inches.

7. The article of claim 6, wherein the ethylene/vinyl acetate copolymer contains about 25–35 weight percent vinyl acetate and the secondary amide is N-erucyl erucamide.

8. The article of claim 5, wherein the ethylene/vinyl acetate copolymer contains about 30–35 weight percent vinyl acetate.

9. The article of claim 8 in the form of tubes or tubing.

* * * * *

UNITED STATES PATENT AND TRADEMARK OFFICE
CERTIFICATE OF CORRECTION

PATENT NO. : 5,399,401
DATED : March 21, 1995
INVENTOR(S) : Richard J. Powell

It is certified that error appears in the above-identified patent and that said Letters Patent is hereby corrected as shown below:

Column 10, line 37, claim 8 - change "5" to --7--.

Signed and Sealed this

Sixth Day of June, 1995

Attest:

BRUCE LEHMAN

*Attesting Officer*     *Commissioner of Patents and Trademarks*